(12) United States Patent
Falahee

(10) Patent No.: US 8,753,376 B2
(45) Date of Patent: *Jun. 17, 2014

(54) POSTERIOR SPINAL RECONSTRUCTION SYSTEM

(75) Inventor: Mark H. Falahee, Ann Arbor, MI (US)

(73) Assignee: Medical Designs, LLC, Ann Arbor, MI (US)

(*) Notice: Subject to any disclaimer, the term of this patent is extended or adjusted under 35 U.S.C. 154(b) by 1194 days.

This patent is subject to a terminal disclaimer.

(21) Appl. No.: 12/559,775

(22) Filed: Sep. 15, 2009

(65) Prior Publication Data

US 2010/0004687 A1    Jan. 7, 2010

Related U.S. Application Data

(63) Continuation of application No. 10/805,900, filed on Mar. 22, 2004, now Pat. No. 7,588,589.

(60) Provisional application No. 60/456,177, filed on Mar. 20, 2003, provisional application No. 60/475,161, filed on Jun. 2, 2003.

(51) Int. Cl.
    *A61B 17/70* (2006.01)

(52) U.S. Cl.
    USPC .......................................................... 606/247

(58) Field of Classification Search
    USPC .............. 606/246–249, 280, 70–71, 281–297
    See application file for complete search history.

(56) References Cited

U.S. PATENT DOCUMENTS

| | | |
|---|---|---|
| 3,426,364 A | 2/1969 | Lumb |
| 4,887,595 A * | 12/1989 | Heinig et al. ................. 606/254 |
| 5,092,893 A | 3/1992 | Smith |
| 5,180,381 A | 1/1993 | Aust et al. |
| 5,403,316 A | 4/1995 | Ashman |
| 5,415,659 A | 5/1995 | Lee et al. |
| 5,603,713 A | 2/1997 | Aust et al. |
| 5,707,372 A | 1/1998 | Errico et al. |
| 5,730,744 A | 3/1998 | Justin et al. |
| 5,733,284 A | 3/1998 | Martin |
| 5,904,682 A | 5/1999 | Rogozinski |
| 6,132,464 A | 10/2000 | Martin |
| 6,554,831 B1 * | 4/2003 | Rivard et al. .................. 606/253 |
| 6,610,091 B1 | 8/2003 | Reiley |
| 6,669,729 B2 | 12/2003 | Chin |
| 6,811,567 B2 | 11/2004 | Reiley |
| 6,974,478 B2 | 12/2005 | Reiley et al. |
| 7,090,698 B2 | 8/2006 | Goble et al. |
| 7,094,238 B2 | 8/2006 | Morrison et al. |
| 2002/0049446 A1 | 4/2002 | Harkey et al. |
| 2003/0153912 A1* | 8/2003 | Graf ................................ 606/61 |

(Continued)

FOREIGN PATENT DOCUMENTS

WO    WO-0189428 A2    11/2001

*Primary Examiner* — Mary Hoffman

(74) *Attorney, Agent, or Firm* — Gifford, Krass, Sprinkle, Anderson & Citkowski, P.C.

(57) ABSTRACT

A system may be fixed in place to stabilize a spinal fusion, or released for dynamic motion, thereby providing stability with flexibility in conjunction with artificial mechanical or plasma discs, or normal physiologic discs. In terms of apparatus, the invention involves pedicle fixation utilizing a superior facet complex (SFC) with soft tissue attachment points. The SFC receives one or more inferior facet gliding arms (IFGAs) and associated joints which permit flexion, extension, lateral bending and/or other movements.

3 Claims, 5 Drawing Sheets

(56) References Cited

U.S. PATENT DOCUMENTS

| | | |
|---|---|---|
| 2003/0163132 A1 | 8/2003 | Chin |
| 2003/0220643 A1 | 11/2003 | Ferree |
| 2004/0049279 A1 | 3/2004 | Sevrain |
| 2004/0097925 A1 | 5/2004 | Boehm et al. |
| 2005/0033434 A1 | 2/2005 | Berry |
| 2005/0055096 A1 | 3/2005 | Serhan et al. |
| 2005/0261682 A1 | 11/2005 | Ferree |

* cited by examiner

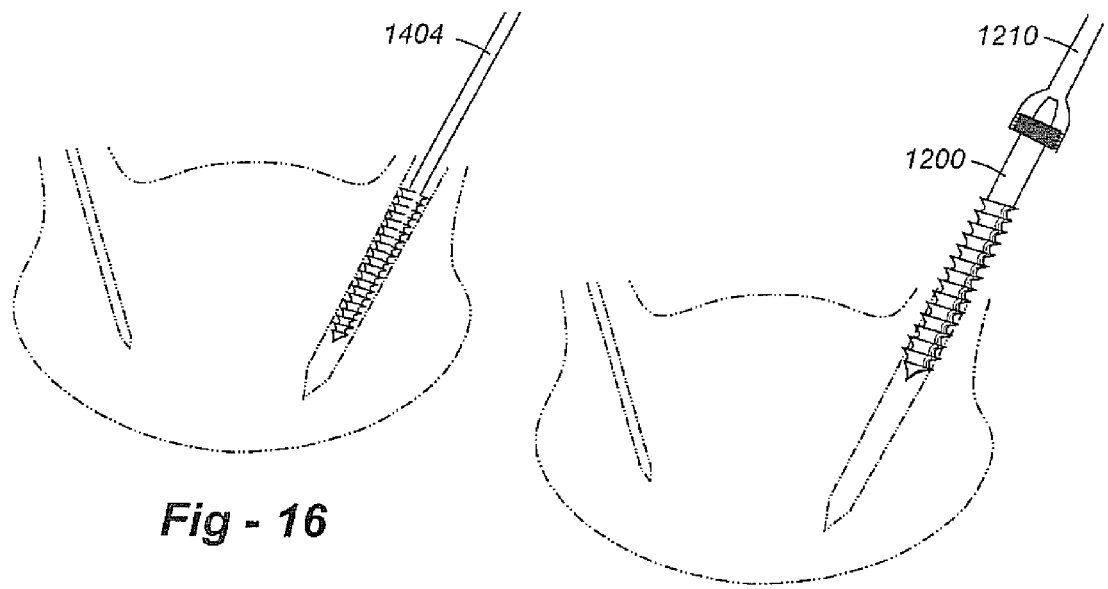
*Fig - 16*
*Fig - 17*
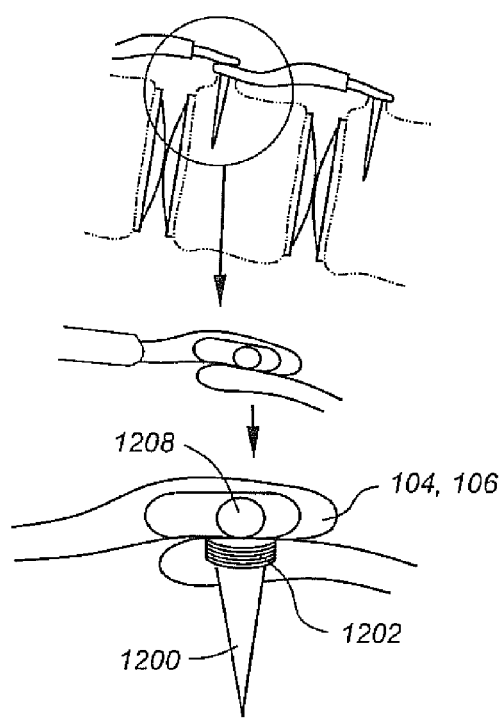
*Fig - 11*
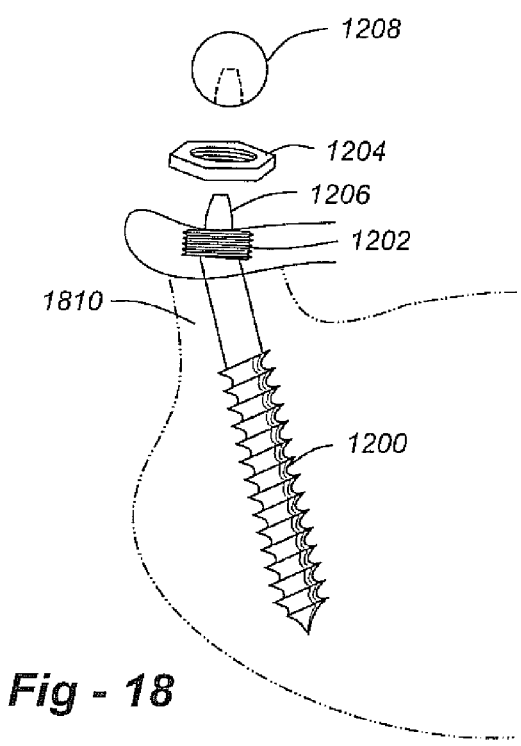
*Fig - 18*

POSTERIOR SPINAL RECONSTRUCTION SYSTEM

REFERENCE TO RELATED APPLICATIONS

This application is a continuation of U.S. patent application Ser. No. 10/805,900, filed Mar. 22, 2004, now U.S. Pat. No. 7,588,589, which claims priority from U.S. Provisional Patent Application Ser. Nos. 60/456,177, filed Mar. 20, 2003 and 60/475,161, filed Jun. 2, 2003, the entire content of each application is incorporated herein by reference.

FIELD OF THE INVENTION

This invention relates generally to spinal reconstruction and, more particularly, to a system that may be fixed in place to stabilize a spinal fusion, or released for dynamic motion.

BACKGROUND OF THE INVENTION

Current posterior spinal reconstruction apparatus involves the use of pedicle screw and rod fixation and facet fixation. The pedicle screw/rod fixation systems are typically used in conjunction with a posterior-lateral and/or intervertebral fusion mechanism. Spinal fixation systems also typically involve some form of fusion. One of the problems with existing approaches is that, due to the fusion involved, the vertebrae are truly mechanically linked to one another, thereby limiting mobility.

SUMMARY OF THE INVENTION

This invention improves upon existing techniques by providing a system that may be fixed in place to stabilize a spinal fusion, or released for dynamic motion, thereby providing stability with flexibility in conjunction with artificial mechanical or plasma discs, or normal physiologic discs.

In terms of apparatus, the invention involves pedicle fixation utilizing a superior facet complex (SFC) with soft tissue attachment points. The SFC receives one or more inferior facet gliding arms (IFGAs) and associated joints which permit flexion, extension, lateral bending and/or other movements.

BRIEF DESCRIPTION OF THE DRAWINGS

FIG. 11 illustrates the accommodation of a gliding socket for a pedicle "ball;"

FIG. 16 shows how, once the SAG is properly positioned, a holding peg drill sleeve is placed into the opposing ends of the guide;

FIG. 17 is a drawing which illustrates the situation after the screws are introduced; and FIG. 18 shows the way the various pieces are assembled onto the anchoring pedicle screw, once in position.

DETAILED DESCRIPTION OF THE INVENTION

Figure 1:
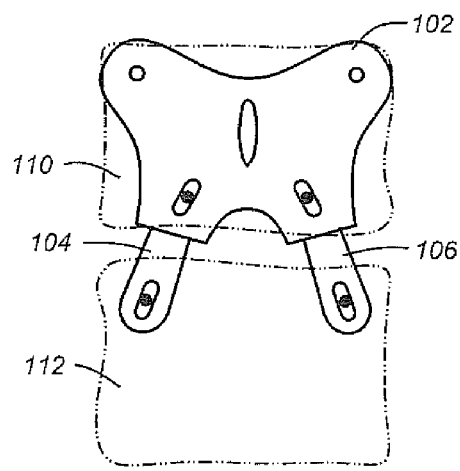
FIG. 1 is a drawing which shows the way in which the SFC and IFGA are positioned on an adjacent vertebra.
Figure 2:
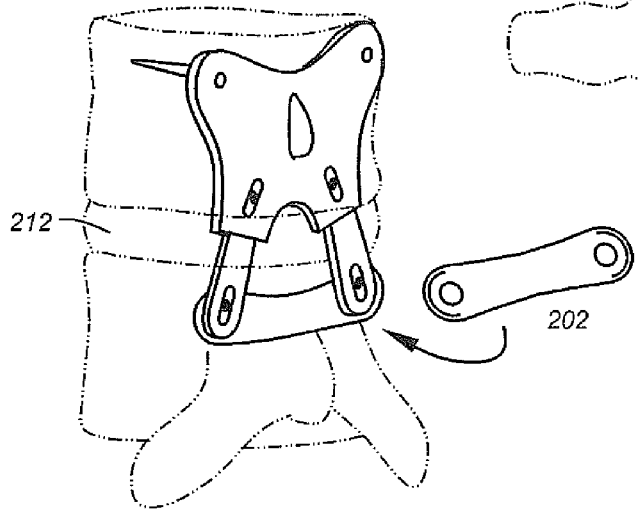
FIG. 2 shows how a link may be provided for the lowest point SFC.

FIG. 1 is a drawing which shows the way in which a superior facet complex (SFC) 102 and inferior facet gliding arms (IFGAs) 104, 106 are positioned on adjacent vertebrae 110, 112. At multiple levels, the IFGAs from an upper level may be attached through the upper points of a corresponding SFC. However, a link 202 may be provided for the lowest point SFC, as shown in FIG. 2. A disk is shown at 212.

Figure 3:
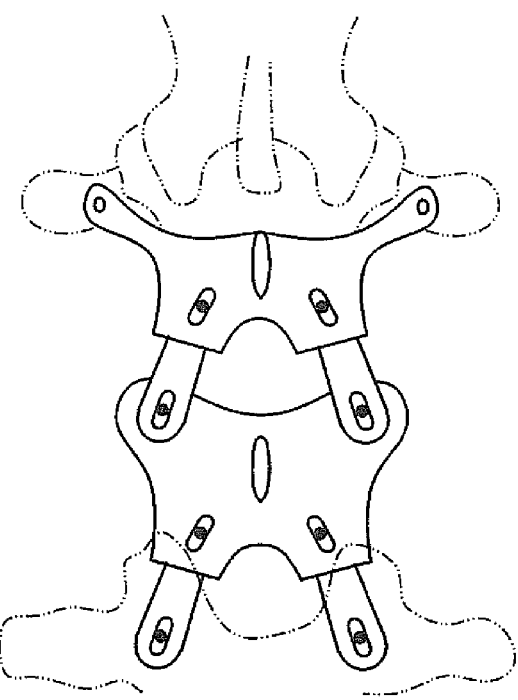
FIG. 3 is a drawing that illustrates how a separate superior pedicle anchoring system may be used to accommodate the most proximal existing inferior/superior facet complex.

The SFC is generally fixed to the superior pedicles of the anatomic vertebrae-disc-vertebrae (VDV) complex, with appropriate contours relative to the joint surface to allow for gliding of the inferior facet. As shown in FIG. 3, a separate superior pedicle anchoring design 302 may be used to accommodate the most proximal existing inferior/superior facet complex. The use of a central pedicle fixation anchor provides an attachment post for the inferior facet to interface with and use a gliding track and stop. Other arrangements may be accommodated, including ball and gliding socket designs, and the like.

Figure 4:
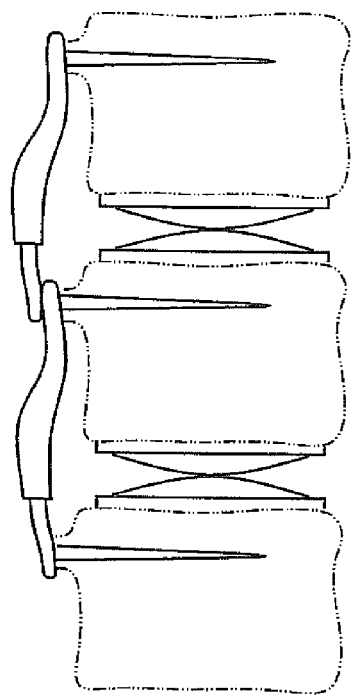
FIG. 4 shows a system according to the invention in a neutral position.
Figure 5:
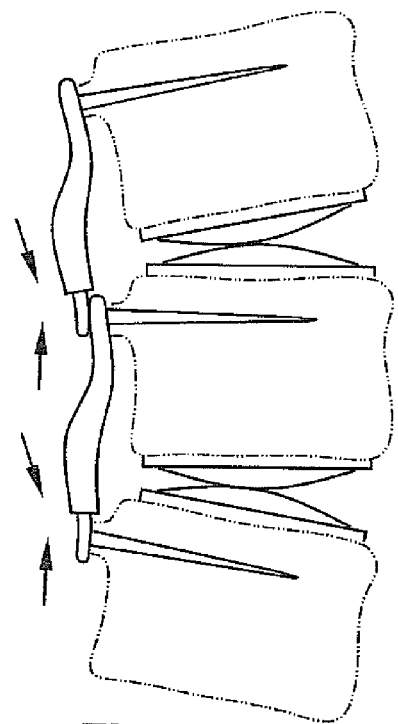
FIG. 5 shows the system and the way in which it facilitates extension.
Figure 6:
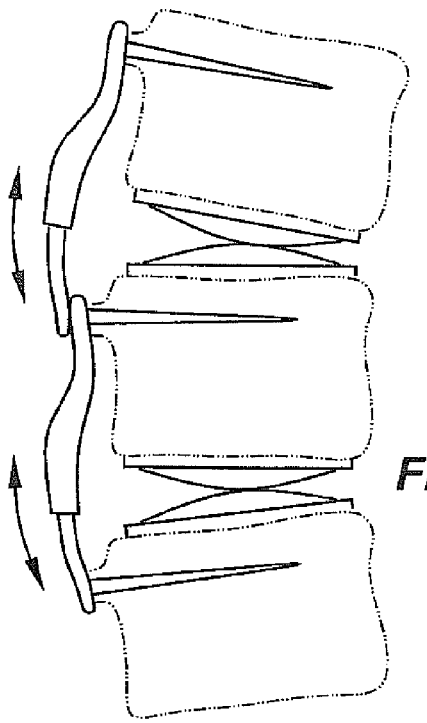
FIG. 6 shows the system and the way in which it facilitates flexion.
Figure 7:
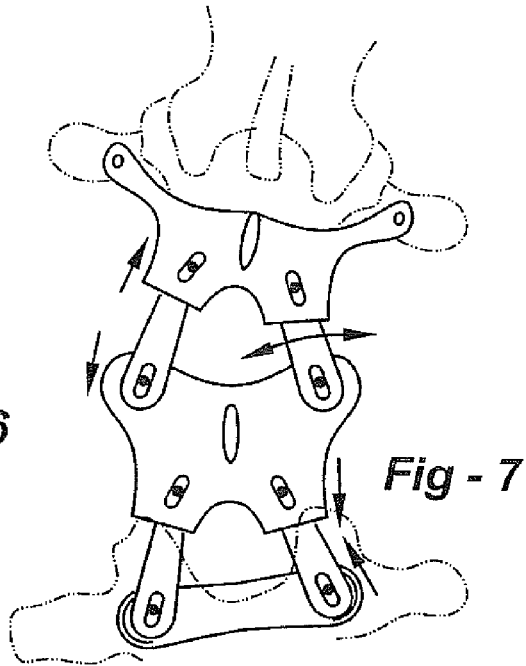
FIG. 7 shows the system and the way in which it facilities side-to-side or lateral bending.
Figure 8A:
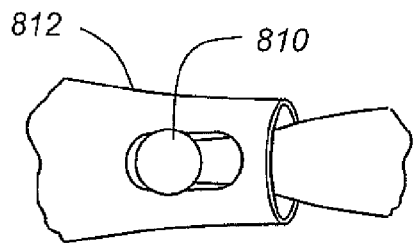
FIG. 8A is a drawing that shows how the IFGAs may use different flexible material.
Figure 8C:
FIG. 8C illustrates multiple degrees of freedom.
Figure 8C:
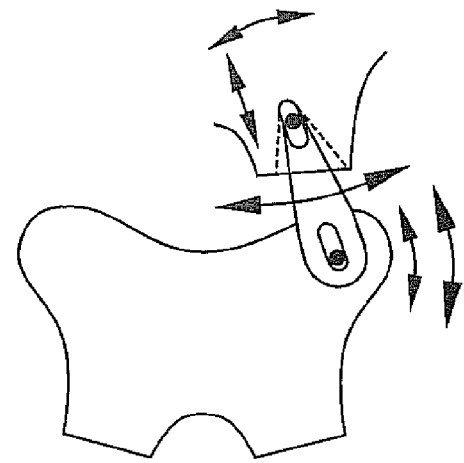
Figure 8B:
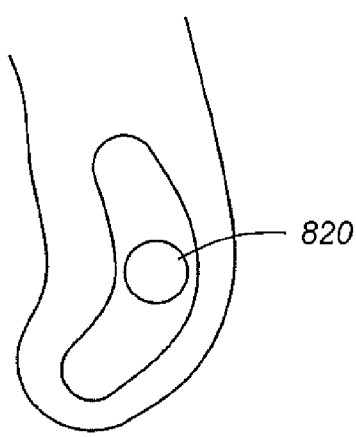
FIG. 8B shows the use of a curved slot.

Overall, the SFC according to the invention is preferably low in profile, and mimics the anatomy it replaces through the use of soft tissue attachment points. FIG. 4 shows the system in a neutral position, whereas FIGS. 5, 6 and 7 respectively show how the components facilitate extension, flexion and side-to-side or lateral bending.

Figure 9:
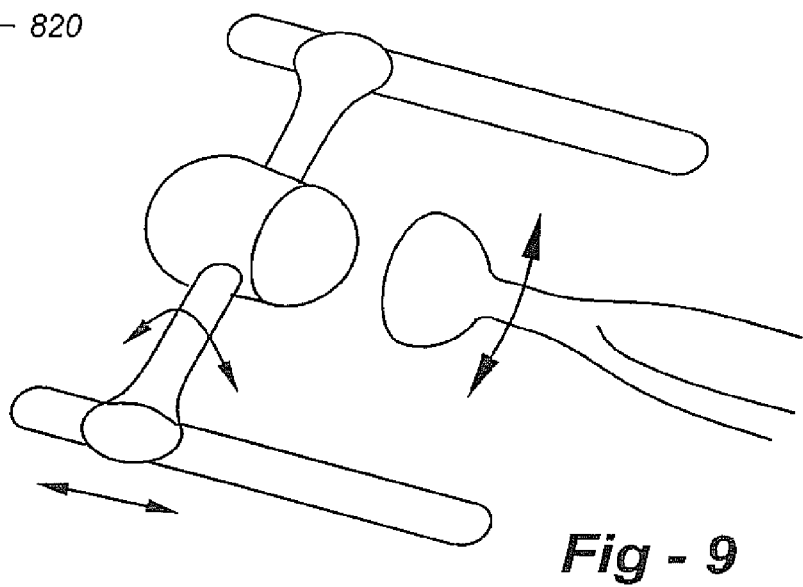
FIG. 9 shows the way in which two pivoting and/or gliding fixation points of the SFCs may extend down to the convex contour of the superior facet below.
Figure 10:
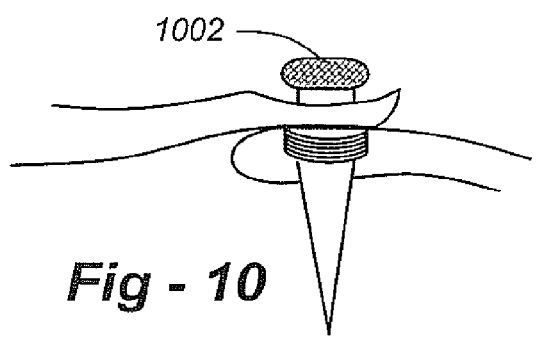
FIG. 10 depicts how a convex gliding surface preferably provides a slot for a pedicle post.

The IFGAs may use stiff or flexible material, attaching two pivoting and/or gliding fixation points of the SFCs, as shown in FIGS. 8 and 9, and extend down to the convex contour of the superior facet below. As shown in FIG. 8A, an end of the IFGA aim 808 snaps onto a gliding peg 810 retained in the SFC 812. The IFGA may feature a curved slot 820, as shown in FIG. 8B, facilitating at least the degrees of freedom depicted in FIG. 8C. The use of a convex gliding surface preferably provides a slot for a pedicle post, as shown in FIG. 10, retained with a locking cap 1002, or a gliding socket for a pedicle "ball" 1208 as shown in FIG. 11. A convex gliding surface is shown at 104, 106, and tapered screw anchor at 1200 with locking mechanism 1202. Varying lengths may be provided according to the invention to mix and match so as to accommodate patient physiology, as appropriate.

Figure 12:
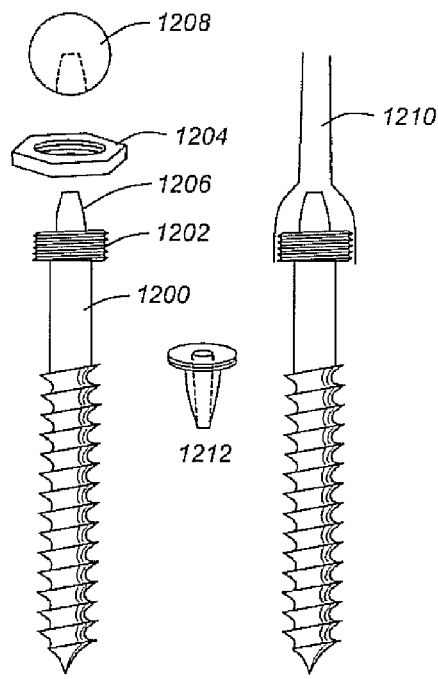
FIG. 12 illustrates the use of anchoring pedicle screws which include a dynamic SFC blocking section, separate blocking nut, as well as a more stable proximal stem and separate IFGA ball.

The anchoring pedicle screws are low in profile, tapered and provide varying diameters and lengths, as appropriate. Different materials, including titanium, may be used for construction. As shown in FIG. 12, the anchoring pedicle screws 1200 include a dynamic SFC locking section 1202, separate locking nut 1204, Morse taper proximal stem 1206 and a separate IFCG ball 1208. A screw holder 1210 fits onto the locking section for placement purposes, in conjunction with a holding peg drill sleeve 1212.

Figure 13:
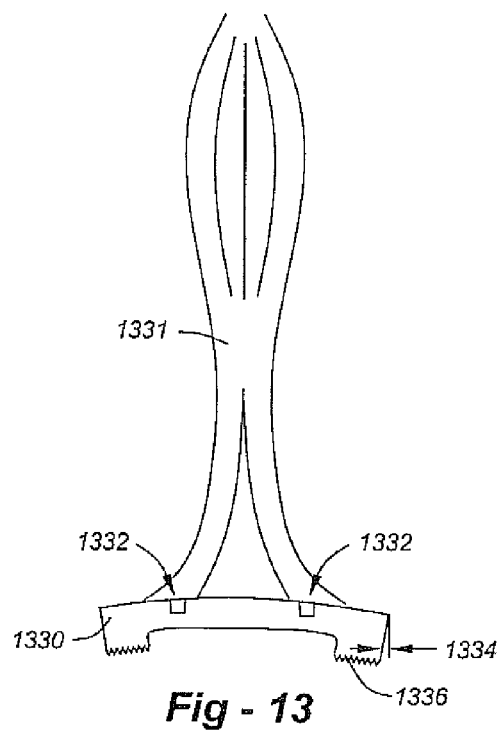
FIG. 13 shows how screws are preferably placed with the use of a symmetrical alignment guide to ensure that they are parallel and aligned in all planes.
Figure 14:
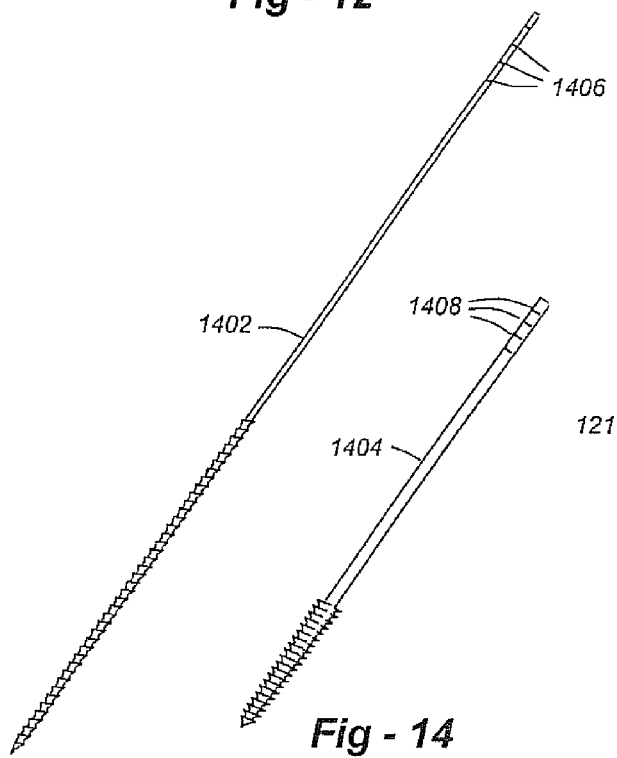
FIG. 14 shows a drill with a tab having depth markers applicable to the invention.

The screws are preferably placed with the use of a symmetrical alignment guide (SAG) 1330 and holder 1331, shown in FIG. 13, to ensure that the anchor screws are parallel and aligned in all planes. A snap-on attachment 1332 may be provided, and the SAG may feature varying angles 1334 and serrated edges 1336. Other instruments include SAGs of varying widths and angles, holding pegs/drill reduction sleeves, drills with depth markings, tapered tabs with markings, feeler probes, screw holder, locking nut holder, and so forth. FIG. 14, for example, shows a drill 1402 and tap 1404 with depth markers 1406, 1408 applicable to the invention.

Figure 15:
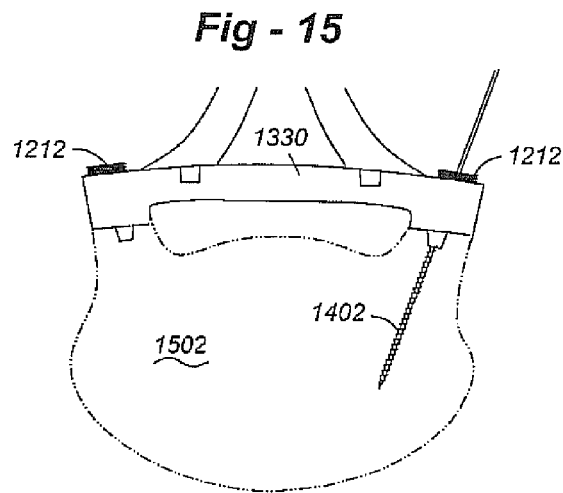
FIG. 15 illustrates the way in which the pedicle screws are introduced into the vertebra using a symmetrical alignment guide.

FIG. 15 illustrates the way in which the pedicle screws are introduced into the vertebrae 1502 using the symmetrical alignment guide 1330. Once the SAG is properly positioned, holding peg drill sleeves 1212 are placed into the opposing ends of the guide, and holes are drilled 1402 and tapped 1404, as shown in FIG. 16, after which the screws 1200 may be introduced as shown in FIG. 17. FIG. 18 shows the way the various pieces are assembled onto the anchoring pedicle screw 1200 once in position, including a toggle 1202 to accommodate different angles, lock nut 1204, and ball 1208. The pedicle is shown at 1210.

In terms of an overall method, the posterior elements are removed, and the soft tissue is released or removed as necessary. Osteophytes are removed as well, as necessary. Any deformity correction not requiring pedicle fixation may be carried out at this stage.

Next the pedicle anchor screws are placed, as discussed above. Temporary distraction, compression is carried out through the pedicle screws as necessary to accommodate the next step. Intercanal work is now done, which may include stenosis, disc removal PLIF (posterior lumbar interbody fusion), artificial disc placement, and so forth. The SFCs are then placed. The most proximal specialized pedicle anchors and complex are placed, along with specialized most distal SFC.

The IFGAs are sized and placed proximal to distal, snapping into the SFC at midpoint of the gliding track, and onto the pedicle anchor (ball) at the midpoint of the inferior facet gliding track or socket.

The individual gliding arms/points are distracted/compressed/fixed or left dynamic, as appropriate. Dynamic function testing is then carried out, followed by soft tissue reattachment to the SFC enclosure.

The system described herein includes numerous advantages over existing approaches including at least the following:

1. Replaces the structural and functional aspects of the posterior elements of the thoracic and lumbar spine.
2. Allows complete removal of posterior elements for maximum access and decompression of neural tissues.
3. Allows maximum removal of arthritic bone and thickened tissues, to maximize correction of spinal deformity.
4. Allows easy access posteriorly, or posterior-lateral to vertebral bodies, disc spaces, and surrounding soft tissues and deformities.
5. Minimizes and possibly eliminates the need for retroperitoneal or anterior approaches to the spine for deformity work, releasing of soft tissue, fusions, or artificial disc replacements.
6. Works in tandem with artificial discs to maximize correction of spinal deformity and stenosis before disc replacement, followed by offering dynamic posterior stability.
7. Designed as a single or multiple level, stackable system, that can be fixed for fusions, or dynamic with natural endpoints, to allow physiologic motion.

The key features include:
1. Mimics anatomic appearance and function.
2. Pedicle fixation of an SFC with soft tissue attachment points.
3. Inferior IFGA and joints allowing flexion, extension, side-to-side bending.
4. Pedicle fixation, triangulation system. Precise symmetrical placement. Fixation point for superior facet complex.
5. Varying sizes and lengths of implant SFC and IFGA to accommodate different sized patients, and deformity situations.
6. Low profile, stackable, lockable.

I claim:

1. Facet joint reconstruction apparatus adapted for fixation to the posterior aspect of a spine having a vertical midline between outward lateral sides, the apparatus comprising:
   a pair of gliding arms, including a first gliding arm disposed on one posterior side of the vertical midline and a second gliding arm disposed on a second posterior side of the vertical midline;
   each gliding arm having an upper end with a first coupling to an upper vertebral body and a lower end with a second coupling to a lower vertebral body;
   each gliding arm having a longitudinal axis that extends laterally outwardly and away from the midline at a non-zero angle;
   wherein, with the apparatus fully assembled and implanted, at least the first couplings of the gliding arms provide a limited degree of axial movement in multiple planes to facilitate flexion, extension, and lateral bending; and
   wherein the second coupling includes a slot on the gliding arm and a pedicle screw with a pin or ball that engages with the slot.

2. Facet joint reconstruction apparatus adapted for fixation to the posterior aspect of a spine having a vertical midline between outward lateral sides, the apparatus comprising:
   a pair of gliding arms, including a first gliding arm disposed on one posterior side of the vertical midline and a second gliding arm disposed on a second posterior side of the vertical midline;
   each gliding arm having an upper end with a first coupling to an upper vertebral body and a lower end with a second coupling to a lower vertebral body;
   each gliding arm having a longitudinal axis that extends laterally outwardly and away from the midline at a non-zero angle;
   wherein, with the apparatus fully assembled and implanted, at least the first couplings of the gliding arms provide a limited degree of axial movement in multiple planes to facilitate flexion, extension, and lateral bending; and
   wherein the first couplings provide a limited degree of pivoting from side to side.

3. Facet joint reconstruction apparatus adapted for fixation to the posterior aspect of a spine having a vertical midline between outward lateral sides, the apparatus comprising:

a pair of gliding arms, including a first gliding arm disposed on one posterior side of the vertical midline and a second gliding arm disposed on a second posterior side of the vertical midline;

each gliding arm having an upper end with a first coupling to an upper vertebral body and a lower end with a second coupling to a lower vertebral body;

each gliding arm having a longitudinal axis that extends laterally outwardly and away from the midline at a non-zero angle;

wherein, with the apparatus fully assembled and implanted, at least the first couplings of the gliding arms provide a limited degree of axial movement in multiple planes to facilitate flexion, extension, and lateral bending; and wherein the upper end of each gliding arm is received by a lower sleeve on either side of a plate.

* * * * *